(12) United States Patent
Zoland et al.

(10) Patent No.: US 8,603,117 B2
(45) Date of Patent: Dec. 10, 2013

(54) PROSTHETIC MESH FOR LAPAROSCOPIC REPAIR OF INGUINAL HERNIA

(75) Inventors: Mark P. Zoland, Scarsdale, NY (US); Joseph Iraci, New Rochelle, NY (US)

(73) Assignee: Conform, LLC, New York, NY (US)

( * ) Notice: Subject to any disclaimer, the term of this patent is extended or adjusted under 35 U.S.C. 154(b) by 0 days.

(21) Appl. No.: 13/453,220

(22) Filed: Apr. 23, 2012

(65) Prior Publication Data

US 2013/0282032 A1 Oct. 24, 2013

(51) Int. Cl.
*A61B 17/08* (2006.01)
(52) U.S. Cl.
USPC ............................ 606/151; 623/23.72
(58) Field of Classification Search
USPC .......... 606/151–158, 213; 602/44; 623/23.64, 623/23.72; 128/898
See application file for complete search history.

(56) References Cited

U.S. PATENT DOCUMENTS

| | | | |
|---|---|---|---|
| 5,141,515 A | 8/1992 | Eberbach | |
| 5,824,082 A * | 10/1998 | Brown | 623/11.11 |
| 5,916,225 A | 6/1999 | Kugel | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,224,616 B1 | 5/2001 | Kugel | |
| 6,280,453 B1 | 8/2001 | Kugel et al. | |
| 6,290,708 B1 | 9/2001 | Kugel et al. | |
| 6,319,264 B1 | 11/2001 | Tormala et al. | |
| 6,565,580 B1 | 5/2003 | Beretta | |
| 6,740,122 B1 | 5/2004 | Pajotin | |
| 7,011,688 B2 | 3/2006 | Gryska et al. | |
| 7,112,209 B2 | 9/2006 | Ramshaw et al. | |
| 2005/0192600 A1 | 9/2005 | Nicolo et al. | |
| 2008/0033461 A1 | 2/2008 | Koeckerling et al. | |
| 2008/0243149 A1 | 10/2008 | Kockerling et al. | |
| 2009/0149875 A1 | 6/2009 | Abele et al. | |
| 2009/0270999 A1 | 10/2009 | Brown | |
| 2010/0241145 A1 | 9/2010 | Cook | |

FOREIGN PATENT DOCUMENTS

| | | | |
|---|---|---|---|
| WO | WO2009003726 | | 1/2009 |
| WO | WO 2010/039978 | * | 4/2010 |

OTHER PUBLICATIONS

Bard* 3DMAX* Mesh, Product Brochure, Davol Inc., 2007.
Parietex ProGrip™ Mesh, Procedure Guide, Covidien, 2008.
Parietex™ Anatomical Mesh, Covidien, 2008.
Promesh Anat T, Preshaped Anatomical Wall Reinforcement Knitted Polypropylene, Surgical IOC, Feb. 2010.
CentriFX Brochure, Atrium Maquet Getinge Group, Feb. 2012.

* cited by examiner

*Primary Examiner* — Ryan Severson
*Assistant Examiner* — Katherine M Shi
(74) *Attorney, Agent, or Firm* — Gordon & Jacobson, PC

(57) ABSTRACT

An implantable prosthetic mesh for repair of an inguinal hernia. The prosthetic mesh includes a conforming soft mesh portion and two displaced portions each having a three dimensional shape and constructed of a stiffer mesh material. The soft mesh portion can be draped over the tissue and spermatic cords, and the two three-dimensional portions formed from the stiffer mesh material are adapted to enter into and be received deep within the respective space defined in the anatomy at each of direct and indirect spaces surrounding the inferior epigastric vessels.

21 Claims, 3 Drawing Sheets

PROSTHETIC MESH FOR LAPAROSCOPIC REPAIR OF INGUINAL HERNIA

BACKGROUND OF THE INVENTION

1. Field of the Invention

This invention relates broadly to surgery. More particularly, this invention relates to surgical meshes for the repair of hernia.

2. State of the Art

Hernias are caused by abnormal defects, tears, or natural openings in membranes, layers of muscle, and/or bone in the body. Such defects may weaken the structural integrity of the defect area and can permit migration of adjacent body structures and/or surrounding tissue (e.g., through an opening), which can result in serious and quite painful symptoms. An inguinal hernia is a protrusion of the abdominal-cavity contents through the inguinal canal and, on each of lateral and contralateral sides of the body, is generally classified as either a direct or indirect hernia defined by its relationship to the inferior epigastric vessels. Direct inguinal hernias occur medial to the inferior epigastric vessels when abdominal contents herniate through a weak spot in the fascia of the posterior wall of the inguinal canal, which is formed by the transversalis fascia. Indirect inguinal hernias occur when abdominal contents protrude through the deep internal ring, lateral to the inferior epigastric vessels. Pantaloon hernias require repair over both the direct and indirect sides.

There are various surgical strategies which are considered in the planning of inguinal hernia repair. Amongst other considerations are mesh use; i.e., whether the biologic tissue will be repaired only to itself or whether a synthetic mesh will be used to assist the repair, and whether the repair will be via an open technique or a closed through-port laparoscopic procedure.

Historically, hernias have been treated by creating an incision through the abdominal wall in an open technique and retracting layers of healthy tissue to expose the defect. The defect was often repaired by sewing strong surrounding muscle over the defect.

Now, with an open technique, it is more common for the surgical repair to be performed in conjunction with a biocompatible mesh that is surgically placed between the layers of tissue at the defect and used to help restore the structural integrity of the repair site. Various types of meshes have been used. Initial biocompatible meshes were flat sheets that were placed at the defect. More recent hernia repair meshes have included additional structure to ostensible aid in the repair.

U.S. Pat. No. 6,565,580 to Beretta teaches a multilayer mesh in which the layers are connected by a flexible band. The lower layer is provided with a hole. In the open technique, which is performed from the outside, the hole was a necessary feature to accommodate the spermatic cord.

U.S. Pat. No. 6,740,122 to Pajotin teaches a mesh with a uniformly stiff three dimensional bowl-shaped structure that conforms to the anatomical shape of the defective wall as presented during an open technique repair. While surgeon's use a commercial embodiment of such mesh in both an open and laparoscopic repair, as a result of the stiffness and shape, the lower border has a tendency to fold up during the laparoscopic repair. This can result in a portion of the defect remaining unsupported. At an unsupported location there is an inherent risk for hernia recurrence.

More recently, it has been preferred by many surgeons to approach the inguinal repair of hernia through a laparoscopic procedure. However, in a laparoscopic repair, the surgery is performed through ports inserted through the abdominal cavity in order to approach the hernia from the interior (opposite) side of the subject anatomy. The mesh is rolled into a tubular form and inserted through a port to the site of the defect. Once the mesh is positioned for repair, it is necessary to retain the mesh so as to prevent displacement and patient discomfort. However, currently available meshes are not ideally adapted for retention on the anatomy from the laparoscopic approach.

SUMMARY OF THE INVENTION

The invention provides an implantable prosthetic mesh for repair of a defect in a muscle or tissue wall, and particularly a defect of an inguinal hernia. The prosthetic mesh is adapted in structure and shape for repair of such hernia in a laparoscopic procedure.

The prosthetic mesh includes a conforming soft mesh portion and two displaced portions having a three dimensional shape and constructed of a stiffer mesh material. The soft mesh portion can be draped over protruding tissue and vessel, and the two three-dimensional portions formed from the stiffer mesh material are adapted to enter into and be received deep within the respective direct and indirect spaces defined in the anatomy surrounding the inferior epigastric vessels. The soft mesh portion, including that portion between the three-dimensional portions, is structured, sized and shaped to accommodate the area surrounding the inferior epigastric vessels and spermatic cord. Importantly, the soft mesh portion exerts very low pressure on the vessels. In view of the structure, size and shape of the mesh, and resulting deep bilateral engagement within the spaces surrounding the inferior epigastric vessels, the mesh contours closely to the anatomy to be retained thereagainst without necessitating additional aid for fixation.

Additional advantages of the invention will become apparent to those skilled in the art upon reference to the detailed description taken in conjunction with the provided figures.

DETAILED DESCRIPTION OF THE PREFERRED EMBODIMENTS

Figure 1:
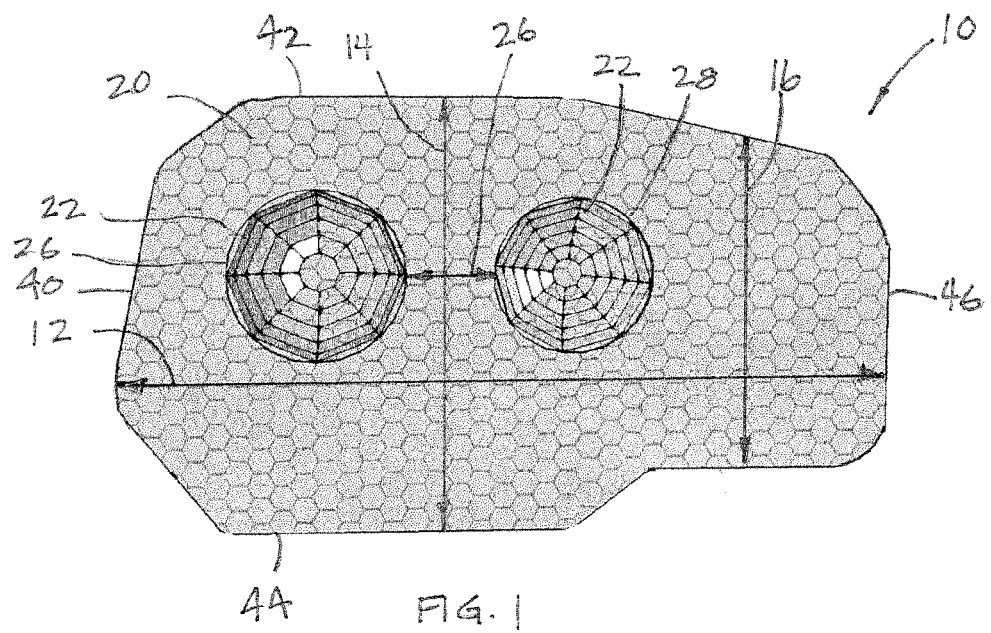
FIG. 1 is a top view of a prosthetic mesh according to a first embodiment of the invention.
Figure 2:
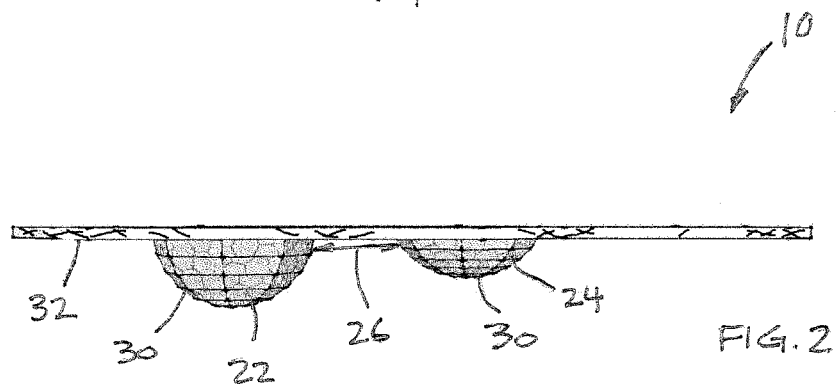
FIG. 2 is a side view of the prosthetic mesh of FIG. 1.
Figure 3:
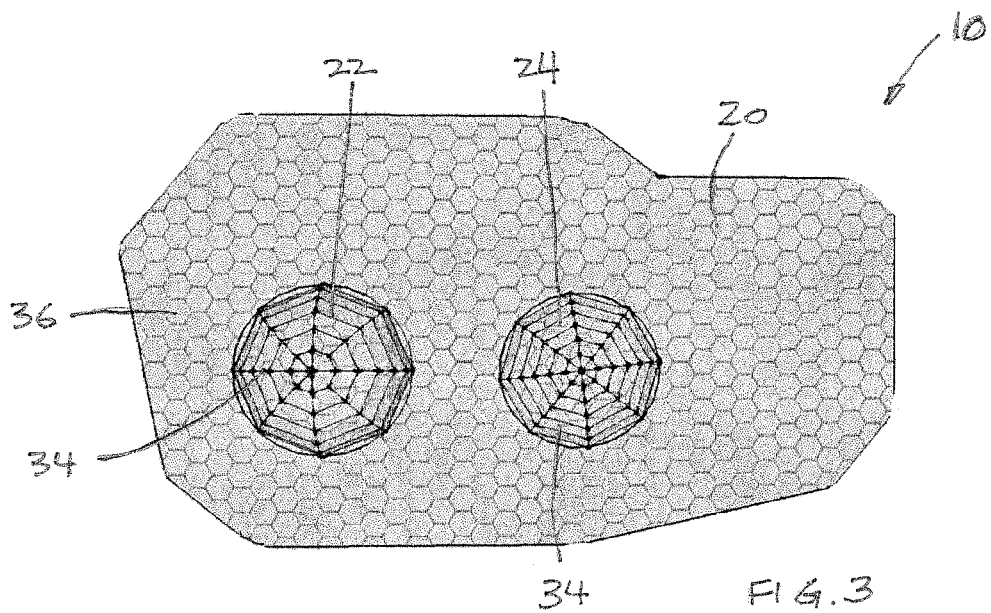
FIG. 3 is a bottom view of prosthetic mesh of FIG. 1.

Referring to FIGS. 1 through 3, a prosthetic mesh 10 for the repair of a defect in muscle or tissue is shown. The mesh is particularly adapted for repair of an inguinal hernia, and more particularly adapted for such repair in a laparoscopic approach in which the defect is approached in a through-port procedure from the opposite side relative to which such defect is otherwise accessed in an open surgical approach.

Figure 4:
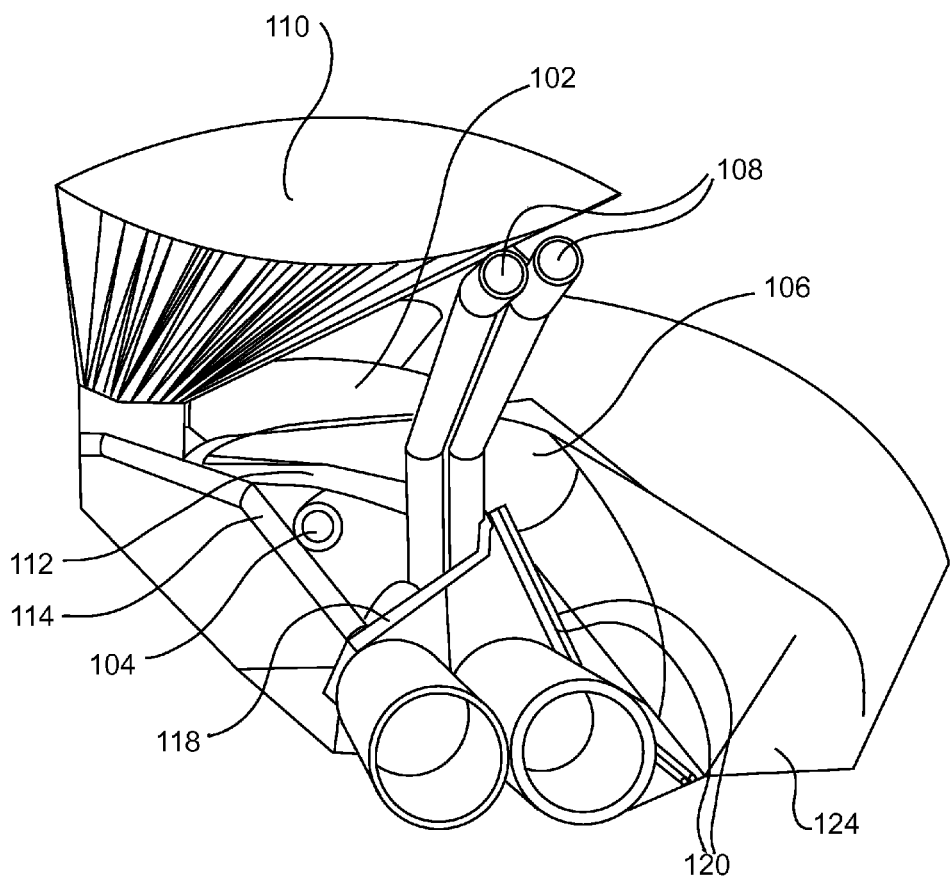
FIG. 4 illustrates the anatomy on which a prosthetic mesh according to the invention is intended to be implanted.
Figure 5:
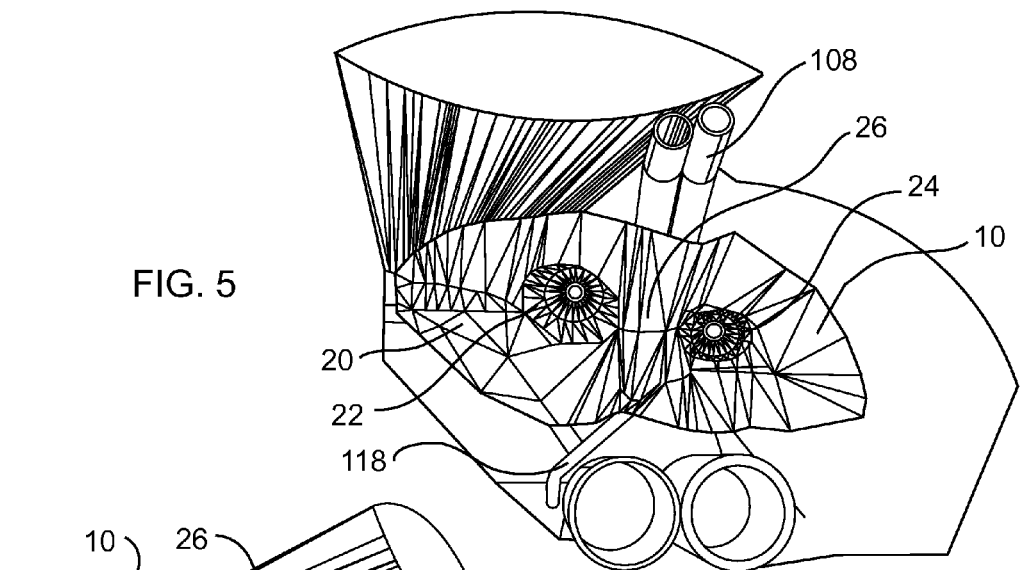
FIG. 5 is a front view illustrating a second embodiment of a prosthetic mesh according to the invention implanted at a hernia repair site.
Figure 6:
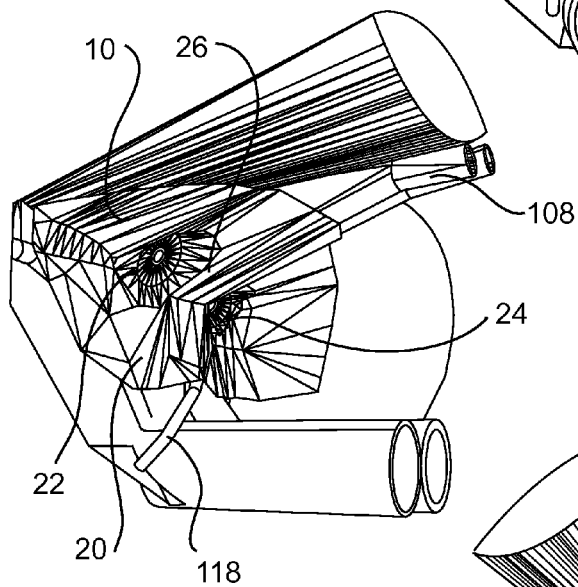
FIG. 6 is a view from the direct side illustrating the prosthetic mesh of FIG. 5 implanted on the anatomy.
Figure 7:
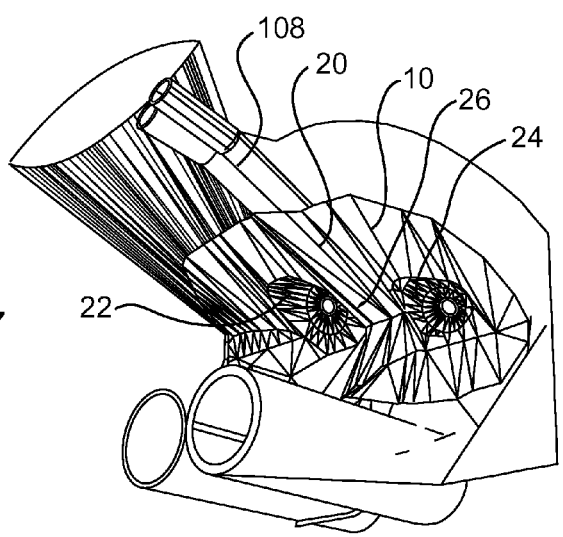
FIG. 7 is a view from the indirect side illustrating the prosthetic mesh of FIG. 5 implanted on the anatomy.

The prosthetic mesh 10 is an oblong structure. With reference to FIG. 4, the mesh 10 has a peripheral size and shape such that it fits over the direct space (or Hesselbach triangle) 102 which is subject to a direct hernia and the femoral ring (over the femoral canal) 104 which is subject to a femoral hernia, both on the medial side of the inferior epigastric vessels 108, and the internal ring 106 defining an indirect space which is subject to an indirect hernia on the lateral side of the inferior epigastric vessels 108. The direct space 102 is defined between the inferior epigastric vessels 108, the medial rectus muscle 110, and the iliopubic tract 112. The femoral ring 104 is defined as the space located between the inferior epigastric vessels 108, the iliopubic tract 112, and the Cooper's ligament 114 and spermatic cord (which comprises both the vas deferens 118 and the gonadal vessels 120). The internal ring (indirect space) 106 is defined as the space on the lateral side of the inferior epigastric vessels 108 anterior to the iliopubic tract 112. The mesh is also sized and shaped to seat above the arcuate band of tissue 124 at the end of the posterior fascia on the lateral side. Furthermore, the mesh 10 is sized to overlap any defect within the defined spaces, preferably by at least 2 cm and more preferably 3-4 cm. Exemplar overall dimensions (e.g., for a large patient) for the prosthetic mesh 10 includes a medial-lateral dimension at 12 of 16±1 cm, a height on the medial-central portion of the mesh at 14 of 10±1 cm, and a height on the lateral side at 16 of 6±1 cm. It is recognized that maximum and minimum dimensions can vary based on the particular peripheral shape selected to define the boundary of the prosthetic mesh. Nevertheless, the shape and size should meet the requirements of fully covering and sufficiently overlapping a tissue defect within the described spaces.

The mesh prosthesis 10 includes a conforming softer first mesh material 20, and two displaced three-dimensional portions 22, 24 of a stiffer second mesh material provided within central openings 26, 28 in the first mesh material. The term 'central' is used to indicate that the openings 26, 28 and portions 22, 24 are located displaced inward from the periphery; that is, the term 'central' does not require that the openings and the three-dimensional portions are located at any mathematical center of the first mesh material 20.

Each of the two three-dimensional portions 22, 24 of the stiffer material have a first side 30 with a convex shape extending outward from the mesh prosthesis on the first side 32 of the mesh prosthesis positioned against the defect, and an opposing second side 34 with a corresponding concave shape defined within the opposing second side 36 of the mesh prosthesis. A first of the three-dimensional portions 22 is adapted to seat in direct space 102 (on the medial side) and a second of the three-dimensional portions 24 is spaced apart a space 26 from the first three-dimensional portion 22 by the softer first mesh material 20 and adapted to seat in the internal ring 106 (on the lateral side). Thus, the space 26 between the first and second three-dimensional portions 22, 24 provides a span of first mesh material 20 that can be draped over the inferior epigastric vessels 108 and spermatic cord 118, 120 (in all dimensions) without impingement thereon.

By way of example only, the following dimensions are provided for an exemplar large size embodiment of a prosthetic mesh 10 according to the invention. The first three-dimensional portion 22 is approximately 2.5±1 cm in diameter and extends 1±½ cm outward from the plane of the first mesh material 20 on the first side 32 of the mesh prosthesis to fit within the contours of direct space 102 on the lateral side. The first three-dimensional portion 22 is displaced 2±1 cm inward from a medial peripheral edge 40, 3.5±1 cm inward from a proximal peripheral edge 42, and 4±1 cm inward from a distal peripheral edge 44. The second three-dimensional portion 24 is approximately 3±1 cm in diameter and extends 1±½ cm outward from the plane of the first mesh material 20 on the first side 32 of the mesh prosthesis to extend into the internal ring 106; that is, the second three-dimensional portion 24 preferably defines a larger volume on the first side 32 of the mesh than the first three-dimensional portion 22 as it is sized for placement into the relatively smaller space of the indirect space 106 (as compared with direct space). The second three-dimensional portion 24 is displaced 5±1 cm inward from the lateral 46 peripheral edge, 3.5±1 cm inward from a proximal peripheral edge 42, and 3.5±1 cm inward from a distal peripheral edge 44. In addition, the larger height on the medial-central portion (relative to the lateral portion) of the prosthetic mesh is adapted to extend over completely over the femoral ring 104. Space 26 between the first and second three-dimensional portions 22, 24 preferably has a width of 1 to 2.5 cm. Dimensions can be proportionately modified for other sizes of the prosthetic mesh. For example, for a medium size prosthetic mesh, the medial-lateral dimension at 12 may be 14±1 cm, and for an extra-large size prosthetic mesh, the medial-lateral dimension at 12 may be 17±1 cm. The various dimensions identified above are then scaled up or down in proportion to the respective medial-lateral dimensions.

As indicated above, the soft first mesh portion 20 is tissue conforming and can be draped over the tissue to conform to the underlying tissue without impingement thereon. As such, the soft mesh portion exerts very low pressure on the tissue, specifically on the vessels and spermatic cord structures. The stiffer three-dimensional portions 22, 24 are adapted in size and shape for specific anatomical 'negative space'. Importantly, the two three-dimensional portions 22, 24 operate as detents with the direct space 102 and the indirect space 106 to self-register the mesh prosthesis 10 in location and orientation at the repair site. In addition, deep engagement of the three-dimensional portions 22, 24 within the anatomy permits the mesh prosthesis 10 to be retained at the repair site without necessitating additional aid for fixation. Further, the mesh takes advantage of using the spermatic cord as a locking pillar, draping the form fitting softer mesh 20 thereover (without wrapping the mesh around the spermatic cord which has been found to result in chronic pain in some patients), and positioning the stiffer three-dimensional portions 22, 24 in close proximity on either side of the spermatic cord to prohibit medial-lateral dislocation. Thus, the need for additional implant material such as screws, tacks, suture, etc., is eliminated. (However, such fixators can be used if preferred by the surgeon.) In view of all of the above, the procedure is expedited.

The softer and stiffer mesh materials 20, 22, 24 may be distinguished by composition of material, thickness of fibers, type of fabric, knit or weave, or forming process. For example, the first mesh materials 20 may be made from various biocompatible polymers, including a knitted polypropylene monofilament mesh fabric. By way of further example, the first mesh material 20 may alternatively be made from other materials which are suitable for tissue reinforcement and/or closure of a defect area, including, but not limited to, PROLENE, MERSELENE, DACRON, TEFLON textile based meshes, microporous polypropylene sheeting CELGARD, and expanded PTFE. By way of example only, the second mesh material for three-dimensional portions 22, 24 may be made from any of the above or in any manner which is provided in a shape-retaining form relative to the first mesh material.

In addition or alternatively, the shape retention may also be provided by heat treating the second mesh material so that the second mesh portions are thermoformed into the three-dimensional portions. In such process, the second mesh is placed into a mold having a desired shape for the three-dimensional portions and heating at an approximate temperature of 100° C. to 200° C. for a period of approximately 5 to 50 minutes, and subsequently coiled with an air flow having an approximate temperature of 15° C. to 30° C. for a period of approximately 5 to 60 minutes. Moreover, the mesh prosthesis can be manufactured from a single material but in which the stiffer three dimensional portions are heat-treated to provide the stiffer, shape-retaining construct of the three-dimensional portions and in which the softer mesh portions are not heat treated to allow the material to maintain an inherent relatively greater flexibility. In such manufacture, the heat-treated and non-heat-treated portions will have different material properties.

In use, the prosthetic mesh 10, even where stiffer, is sufficiently flexible to be rolled into a tubular form of suitable size to be advanced through a 10 mm laparoscopic port. Once in a tubular form, the prosthetic mesh is inserted into a laparoscopic port and advanced to the site of a muscle or tissue defect. Uniformly stiff meshes are more difficult to feed into and advance through the port as a result of the non-giving construct. The present mesh, having a majority of softer relatively flexible mesh, is substantially easier to insert and advance through the port. The mesh is subsequently advanced out of the port and maneuvered with the flexible expanse 26 of the soft first mesh portion 20 between the three dimensional portions 22, 24 draped across the epigastric vessels 108 and spermatic cord 118, 120 and the first three-dimensional portion 22 located on the medial side and seated convex side down within the direct space 102, and the second three-dimensional portion 24 located on the lateral side and seated convex side down within the indirect space 106. If necessary, the softer first portion 20 of the prosthetic mesh can be smoothed over the tissue. Optionally, but not necessarily, aid for fixation can be used if deemed useful by the surgeon. However, it should again be appreciated that the deep seating of the two three-dimensional portions within the anatomical negative space provides sufficient retention in most repairs. Additionally, the structure allows a lower and softer border that is conforming to the tissue (i.e., will not bunch) and will define a seal. This is important as, in distinction from an open procedure, there is no anatomical structure at which to tack the lower border of the mesh when implanted in the laparoscopic approach.

There have been described and illustrated herein embodiments of a prosthetic mesh suitable for laparoscopic repair of a inguinal hernia. While particular embodiments of the invention have been described, it is not intended that the invention be limited thereto, as it is intended that the invention be as broad in scope as the art will allow and that the specification be read likewise. Thus, while particular materials have been disclosed for different portions of the mesh, it will be appreciated that other material for the respective softer and stiffer portions of the prosthetic mesh may be used as well. In addition, while particular shapes of a prosthetic mesh has been disclosed, it will be understood that various other shapes for surrounding the direct and indirect hernia spaces, including shapes that are more contoured, more round, or more rectangular, or more angular, can be used. Thus, while FIGS. 1-3 and 5-7 illustrate different peripheral shapes for a prosthetic mesh according to the invention, each has the common features described herein. Also, while various preferred dimensions have been disclosed, it will be recognized that other dimensions suitable for allowing the prosthetic mesh to cover and extend beyond the defect may be utilized. That is, while a prosthetic mesh for placement over a right side of the human body is shown, a mirror image prosthetic mesh is hereby recognized for placement over the contralateral left side. In addition, while it is preferred that the second three-dimensional portion define a larger volume than the first three-dimensional portion, it is appreciated that both the first and second three-dimensional portions may be of a common size or that even the first three-dimensional portion may be of a larger size than the second three-dimensional portion. Moreover, while the three-dimensional portions are shown generally having a round periphery, each may have a shape other than round designed to provide suitable or optimal fit within the designated anatomical spaces. It will therefore be appreciated by those skilled in the art that yet other modifications could be made to the provided invention without deviating from its scope as claimed.

What is claimed is:

1. A method of repairing a tissue defect in a patient, the patient having on a medial side a direct space located between inferior epigastric vessels, a medial rectus muscle, and an iliopubic tract and a femoral ring defined between the inferior epigastric vessels, the iliopubic tract, and a spermatic cord, and on a lateral side an indirect space defined as lateral to the inferior epigastric vessels and anterior to the iliopubic tract, the method comprising:
   a) providing a prosthetic mesh having a relatively soft conforming first mesh material, and first and second three-dimensional portions of a stiffer second mesh material that are displaced from each other, each of the first and second three-dimensional portions having a first convex surface and an opposing second concave surface; and
   b) placing the first mesh material over the spermatic cord and the first and second three-dimensional portions at the direct and indirect spaces, respectively,
       wherein the convex surfaces of the first and second three-dimensional portions extend into the direct and indirect spaces to thereby anchor the prosthetic mesh relative to the tissue defect.

2. A method according to claim 1, further comprising:
using the spermatic cord as a pillar to prevent medial-lateral dislocation of the prosthetic mesh.

3. A method according to claim 1, further comprising
conforming said first mesh material over the inferior epigastric vessels and the spermatic cord.

4. A method according to claim 1, wherein:
said prosthetic mesh is asymmetric such that one of said first and second three-dimensional portions is larger than the other of said first and second three-dimensional portions.

5. A method according to claim 1, wherein:
said second three-dimensional portion is located lateral of said first three-dimensional portion.

6. A method according to claim 1, wherein:
said first and second three-dimensional portions are displaced from each other by 1 to 2.5 cm.

7. A method according to claim 6, wherein:
said first three-dimensional portion has a diameter of 2.5±1 cm,
said second three-dimensional portion has a diameter of 3.0±1 cm, and
said first and second three-dimensional portions are displaced from each other in a medial-lateral dimension by 1-2.5 cm.

8. A method according to claim 1, wherein:
said first three-dimensional portion has a diameter of 2.5±1 cm,
said second three-dimensional portion has a diameter of 3.0±1 cm, and
said first and second three-dimensional portions are displaced from each other in a medial-lateral dimension by 1-2.5 cm.

9. A method according to claim 1, wherein:
the first and second three-dimensional portions are displaced from each other in a medial-lateral direction, and the provided prosthetic mesh is asymmetric in the medial-lateral direction.

10. A method according to claim 1, wherein:
the first mesh material has first and second central openings, and the first and second three-dimensional portions are coupled within the first and second central openings, respectively.

11. A method of repairing a tissue defect in a patient, the patient having on a medial side a direct space located between inferior epigastric vessels, a medial rectus muscle, and an iliopubic tract, and a femoral ring defined between the inferior epigastric vessels, the iliopubic tract, and a spermatic cord, and on a lateral side an indirect space defined as lateral to the inferior epigastric vessels and anterior to the iliopubic tract, the method comprising:
   a) providing a prosthetic mesh having first and second three-dimensional portions, each with a convex side, that are displaced from each other by a third mesh portion, each of said first and second three-dimensional portions having a stiffer mesh construction than said third mesh portion, the prosthetic mesh provided in a rolled form;
   b) inserting the rolled mesh into a laparoscopic port;
   c) advancing the rolled mesh out of the port to the site of tissue defect; and
   d) maneuvering the mesh so that,
      the first three-dimensional portion is located on the medial side and seated convex side down within the direct space,
      the second three-dimensional portion is located on the lateral side and seated convex side down within the indirect space, and
      the third mesh portion is draped across the epigastric vessels and spermatic cord.

12. A method according to claim 11, wherein:
said first and second three-dimensional portions are displaced from each other by 1 to 2.5 cm.

13. A method according to claim 12, wherein:
said first three-dimensional portion has a maximum diameter of 2.5±1 cm,
said second three-dimensional portion has a maximum diameter of 3.0±1 cm, and
said first and second three-dimensional portions are displaced from each other in a medial-lateral dimension by 1-2.5 cm.

14. A method according to claim 11, wherein:
said first three-dimensional portion has a maximum diameter of 2.5±1 cm,
said second three-dimensional portion has a maximum diameter of 3.0±1 cm, and
said first and second three-dimensional portions are displaced from each other in a medial-lateral dimension by 1-2.5 cm.

15. A method of repairing a tissue defect in a patient, the patient having on a medial side a direct space located between inferior epigastric vessels, a medial rectus muscle, and an iliopubic tract and a femoral ring defined between the inferior epigastric vessels, the iliopubic tract, and a spermatic cord, and on a lateral side an indirect space defined as lateral to the inferior epigastric vessels and anterior to the iliopubic tract, the method comprising:
   a) providing a prosthetic mesh having a relatively soft tissue conforming first mesh material, and stiffer first and second convex mesh portions extending from the first mesh material and which are displaced from each other by the first mesh material; and
   b) placing the first mesh material over the spermatic cord, and the first and second convex mesh portions into the direct and indirect spaces, respectively.

16. A method according to claim 15, further comprising:
inserting the prosthetic mesh into a laparoscopic port; and
advancing the prosthetic mesh out of the port to the site of tissue defect,
wherein said providing includes providing the prosthetic mesh in a rolled form.

17. A method according to claim 15, wherein:
the provided prosthetic mesh is asymmetric such that the first convex mesh portion is smaller than the second convex mesh portion.

18. A method according to claim 15, wherein:
the first and second convex mesh portions are displaced from each other in a medial-lateral direction, and the provided prosthetic mesh is asymmetric in the medial-lateral direction.

19. A method according to claim 15, further comprising:
using the spermatic cord as a pillar to prevent medial-lateral dislocation of the prosthetic mesh.

20. A method according to claim 15, wherein:
the first and second convex mesh portions are displaced from each other by 1 to 2.5 cm.

21. A method according to claim 20, wherein:
the first convex mesh portion has a maximum diameter of 2.5±1 cm,
the second convex mesh portion has a maximum diameter of 3.0±1 cm, and
the first and second convex mesh portions are displaced from each other in a medial-lateral dimension by 1-2.5 cm.

* * * * *